(12) United States Patent
Feldkamp

(10) Patent No.: US 9,687,169 B2
(45) Date of Patent: Jun. 27, 2017

(54) SYSTEM, CONTROLLER, AND METHOD FOR DETERMINING CONDUCTANCE OF AN OBJECT

(71) Applicant: Kimberly-Clark Worldwide, Inc., Neenah, WI (US)

(72) Inventor: Joseph R. Feldkamp, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1141 days.

(21) Appl. No.: 13/660,236

(22) Filed: Oct. 25, 2012

(65) Prior Publication Data

US 2013/0151186 A1    Jun. 13, 2013

Related U.S. Application Data

(60) Provisional application No. 61/568,224, filed on Dec. 8, 2011.

(51) Int. Cl.
*A61B 5/053* (2006.01)
*G01R 27/02* (2006.01)
*G01N 27/02* (2006.01)

(52) U.S. Cl.
CPC ............ *A61B 5/053* (2013.01); *A61B 5/0531* (2013.01); *G01N 27/026* (2013.01); *G01R 27/02* (2013.01)

(58) Field of Classification Search
CPC ............ G01R 27/2611; G01R 27/3006; G01R 27/3658; A61B 2560/0431;

(Continued)

(56) References Cited

U.S. PATENT DOCUMENTS 4,688,580 A    8/1987  Ko et al.
4,833,393 A *  5/1989  Wetzel .................... 324/678
(Continued)

FOREIGN PATENT DOCUMENTS

EP    0826972 A2    3/1998
GB     630638       6/1947
(Continued)

OTHER PUBLICATIONS

Reimann, "Nuclear magnetic resonance field discriminator using digital techniques", Journal of Applied Mathematics and Physics, 1967, pp. 549-556, vol. 18.

(Continued)

*Primary Examiner* — John Breene
*Assistant Examiner* — Jeffrey Aiello
(74) *Attorney, Agent, or Firm* — Armstrong Teasdale LLP

(57) ABSTRACT

A system for determining a conductance of an object includes a sensor configured to emit an electromagnetic field when an excitation signal is received, wherein the electromagnetic field interacts with the object when the object is positioned within the electromagnetic field. A signal processing circuit is coupled to the sensor and configured to provide an adjustable capacitance to the sensor to adjust a phase angle of a current flowing through the sensor, to generate a voltage measurement representative of a voltage across the sensor, and to generate a current measurement representative of the current flowing through the sensor. A controller is coupled to the signal processing circuit and configured to calculate an admittance of the sensor based on the voltage measurement and the current measurement, and to determine a conductance of the object based on the calculated admittance of the sensor.

22 Claims, 7 Drawing Sheets

(58) Field of Classification Search
CPC .... A61B 2560/0462; A61B 2560/0223; A61B 2560/053; A61B 5/06; A61B 2034/2051; A61B 2562/0223; A61B 5/053; G06F 1/00; G01N 27/24; G01N 27/72; A61F 2002/3067
USPC ...... 324/228, 722, 236, 652, 655; 702/1, 85, 702/88, 57
See application file for complete search history.

(56) References Cited

U.S. PATENT DOCUMENTS

| | | | |
|---|---|---|---|
| 4,850,372 A | 7/1989 | Ko et al. | |
| 5,069,223 A | 12/1991 | McRae | |
| 5,793,214 A | 8/1998 | Wakamatsu | |
| 6,259,259 B1* | 7/2001 | Raffalt et al. | 324/650 |
| 6,336,045 B1 | 1/2002 | Brooks | |
| 6,388,453 B1* | 5/2002 | Greer | 324/667 |
| 6,413,223 B1 | 7/2002 | Yang et al. | |
| 6,517,482 B1 | 2/2003 | Elden et al. | |
| 6,541,963 B2 | 4/2003 | Mednikov et al. | |
| 6,768,921 B2 | 7/2004 | Organ et al. | |
| 7,358,720 B1* | 4/2008 | Maier | 324/207.26 |
| 7,918,801 B2 | 4/2011 | Cochran | |
| 7,930,128 B2 | 4/2011 | Beard | |
| 2003/0112015 A1* | 6/2003 | Takakamo et al. | 324/525 |
| 2004/0199232 A1 | 10/2004 | Wallace et al. | |
| 2004/0243019 A1 | 12/2004 | Graovac et al. | |
| 2006/0017450 A1 | 1/2006 | Thibedean et al. | |
| 2006/0036382 A1* | 2/2006 | Paz | G01R 27/02 702/76 |
| 2006/0151815 A1 | 7/2006 | Graovac et al. | |
| 2006/0264732 A1* | 11/2006 | Wu | 600/407 |
| 2007/0035203 A1* | 2/2007 | Bromfield | 310/311 |
| 2007/0108972 A1 | 5/2007 | Blew et al. | |
| 2009/0091314 A1* | 4/2009 | Karenowska | G01D 5/20 324/207.16 |
| 2009/0102450 A1* | 4/2009 | Da Silva et al. | 324/72 |
| 2009/0140727 A1* | 6/2009 | Rollins | G01B 7/023 324/207.16 |
| 2009/0171237 A1 | 7/2009 | Campbell | |
| 2009/0217749 A1* | 9/2009 | Torigoe et al. | 73/149 |
| 2010/0056880 A1 | 3/2010 | Cho et al. | |
| 2010/0219841 A1* | 9/2010 | Feldkamp et al. | 324/655 |
| 2011/0068807 A1* | 3/2011 | Kesil | G01N 27/023 324/633 |
| 2013/0021045 A1* | 1/2013 | Virnich et al. | 324/686 |
| 2013/0076343 A1* | 3/2013 | Carpenter et al. | 324/202 |

FOREIGN PATENT DOCUMENTS

| | | |
|---|---|---|
| GB | 2449273 | 11/2008 |
| JP | 08015341 A | 1/1996 |

OTHER PUBLICATIONS

International Search Report and Written Opinion for PCT/IB2012/056128 dated Mar. 11, 2013; 10 pages.
International Search Report and Written Opinion for PCT/IB2013/058621 dated Feb. 11, 2014; 12 pages.

* cited by examiner

SYSTEM, CONTROLLER, AND METHOD FOR DETERMINING CONDUCTANCE OF AN OBJECT

CROSS-REFERENCE TO RELATED APPLICATION

This application claims the benefit of U.S. Provisional Application No. 61/568,224 filed Dec. 8, 2011, which is incorporated herein by reference in its entirety.

FIELD

The field of the invention relates generally to monitoring systems and more specifically to system, controller, and method for determining conductance of an object or material.

BACKGROUND

Some known measurement systems measure a conductivity of a specimen of interest by placing electrodes into contact with the specimen. A voltage is applied to the electrodes and a resulting current is measured. The conductivity is then computed from the measured current. In some cases, many electrodes are attached to the specimen so that a type of imaging is made possible, provided that conductivity varies spatially through the specimen. This latter condition is true for geological specimens and human tissue specimens.

An alternative is to generate eddy currents within the specimen through inductive coupling to an external coil. The eddy currents exist in proportion to the local conductivity of the material and can be detected in a number of ways. For example, an amount of electrical energy dissipated in the coil may be measured when the coil is placed near a specimen.

The eddy currents are typically generated using a probe or a sensor that oscillates in a resonance state. A phase-locked-loop (PLL) circuit may be included in the probe to automatically tune the probe such that the probe is maintained in the resonant state. In addition, such probes may require additional components to maintain the resonant state or to detect the energy dissipated, such as a peak detector and/or a variable resistor. The PLL circuitry and the additional components may undesirably increase a size and a cost of the probe.

Thus, there remains a need for systems and methods that non-invasively determine the conductance of an object in a cost-effective, accurate, and efficient manner.

SUMMARY

In one aspect, a system for determining a conductance of an object generally comprises a sensor configured to emit an electromagnetic field when an excitation signal is received, wherein the electromagnetic field interacts with the object when the object is positioned within the electromagnetic field. A signal processing circuit is coupled to the sensor and configured to provide an adjustable capacitance to the sensor to adjust a phase angle of a current flowing through the sensor, to generate a voltage measurement representative of a voltage across the sensor, and to generate a current measurement representative of the current flowing through the sensor. A controller is coupled to the signal processing circuit and configured to calculate an admittance of the sensor based on the voltage measurement and the current measurement, and to determine a conductance of the object based on the calculated admittance of the sensor.

In another aspect, a method of determining a conductance of an object generally comprises emitting an electromagnetic field towards an object such that the electromagnetic field interacts with the object. A phase angle of a current flowing through the sensor is adjusted using an adjustable capacitive element coupled to the sensor. A voltage measurement representative of a voltage across the sensor and a current measurement representative of the current flowing through the sensor are generated. An admittance of the sensor is calculated based on the voltage measurement and the current measurement, and a conductance of the object is determined based on the calculated admittance of the sensor.

In still another aspect, a controller for determining a conductance of an object generally comprises a processor and a memory device coupled to the processor. The memory device is configured to store a plurality of program modules including a phase angle calculator module executable by the processor to receive a current measurement representative of a current flowing through a sensor, and calculate a phase angle of the current flowing through the sensor. The program modules also include an impedance calculator module executable by the processor to receive the current measurement, receive a voltage measurement representative of a voltage across the sensor, and calculate an impedance of the sensor based on the current measurement and the voltage measurement. The program modules further include an admittance calculator module executable by the processor to calculate an admittance of the sensor based on the calculated phase angle and the calculated impedance, and a conductance calculator module executable by the processor to determine a conductance of the object based on the calculated admittance of the sensor.

BRIEF DESCRIPTION OF THE DRAWINGS

Corresponding reference characters indicate corresponding parts throughout the drawings.

DETAILED DESCRIPTION OF THE DRAWINGS

Figure 1:
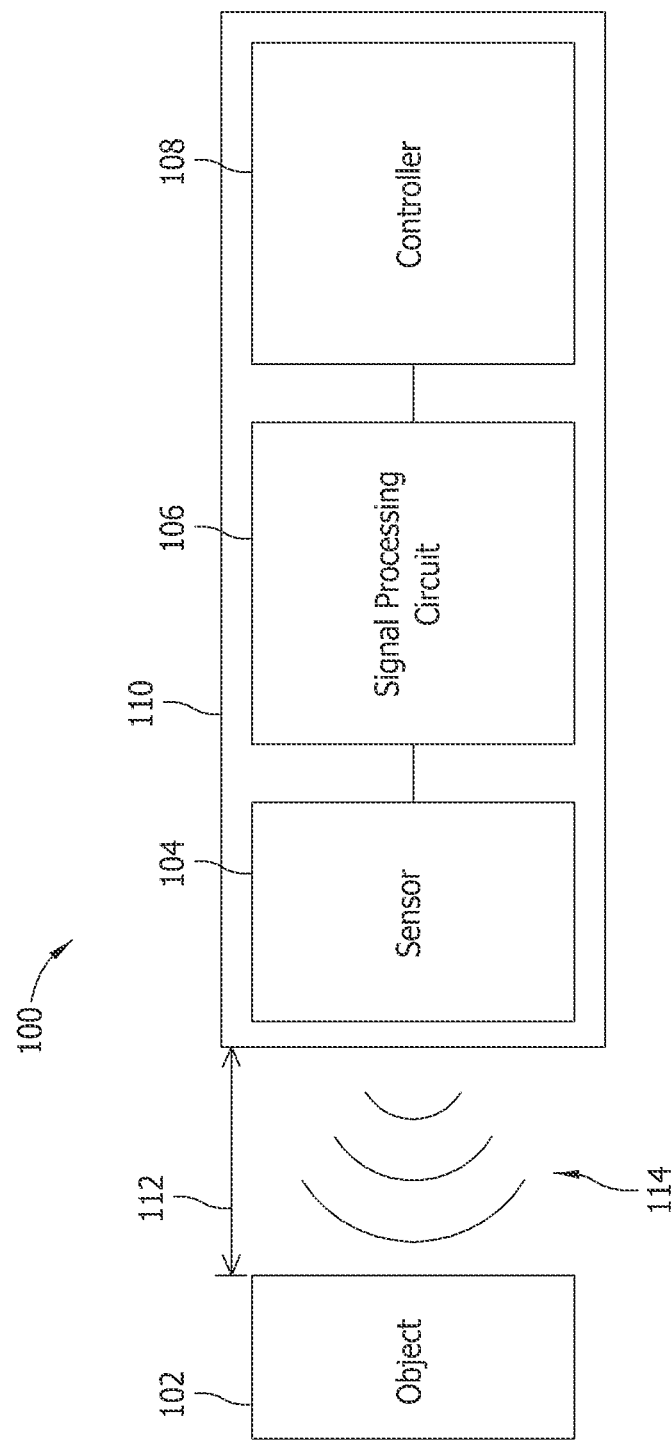
FIG. 1 is a block diagram of one embodiment of a monitoring system that can be used to determine a conductance of an object.

FIG. 1 is a block diagram of one suitable embodiment of a monitoring system, indicated generally at 100, that can be used to determine or monitor a conductance of an object 102. In one suitable embodiment, the monitoring system 100 is used to non-invasively determine and/or monitor a conductance (or conductivity) at one or more locations on a person's body for use in determining a condition or diagnosing a disease of the person, e.g., vascular disease.

The monitoring system 100 includes a sensor 104 coupled to a signal processing circuit 106, and a controller 108 coupled to the signal processing circuit. In one suitable embodiment, the monitoring system 100 may be enclosed within a housing 110 to protect the components of the system. The housing 110 may be positioned in close proximity to the object 102 such that a gap 112 is defined between the sensor 104 and the object 102.

During operation, the signal processing circuit 106 generates a fixed frequency excitation signal and transmits the excitation signal to the sensor 104. The excitation signal causes the sensor 104 to emit an electromagnetic field, indicated generally at 114. When the sensor 104 is placed in close proximity to the object 102, the field 114 traverses the gap 112 and interacts with the object, causing eddy currents to be formed within the object. The interaction of the field 114 and the object 102 usually causes a shift in the phase angle of a signal received from the sensor 104 (e.g., a current flowing through the sensor) due to stray capacitance developing across the sensor while the sensor is in proximity to the object being tested or monitored. Specifically, the current through the sensor 104 and the voltage across the sensor may not reach their respective maximum values at the same time. Accordingly, the phase angle refers to the difference between the time that the current flowing through the sensor 104 reaches the maximum value and the time that the voltage across the sensor reaches the maximum value. A zero phase angle indicates a resonant condition of the sensor 104.

In addition, the signal received from the sensor 104 may be attenuated, causing an amplitude of the signal to be reduced as compared to an amplitude of the excitation signal. The attenuation of the signal causes an effective impedance to be induced to the sensor 104. As described more fully herein, the signal processing circuit 106 measures the current and the voltage of the signal received from the sensor 104 and transmits the measured current and voltage to the controller 108.

The controller 108 detects the phase angle of the signal received from the sensor 104 and detects an impedance of the sensor based on the voltage and the current measurements received from the signal processing circuit 106. In addition, the controller 108 calculates an admittance of the sensor 104 and uses the calculated admittance to determine the conductance of the object 102. The conductance of the object 102 can be used to determine one or more characteristics or conditions of the object.

Figure 2A:
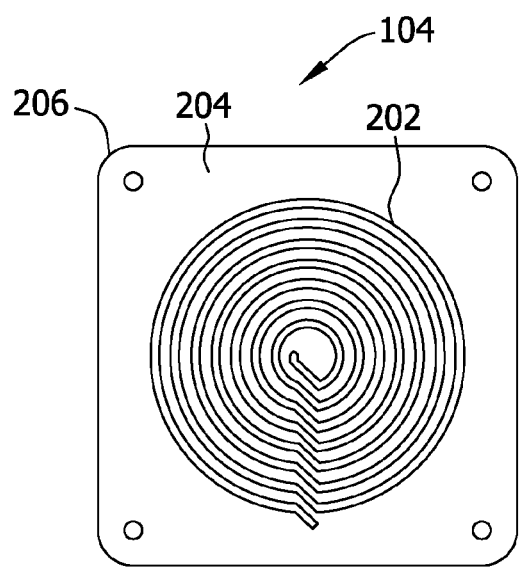
FIG. 2A is a top view of a sensor suitable for use with the monitoring system of FIG. 1.
Figure 2B:
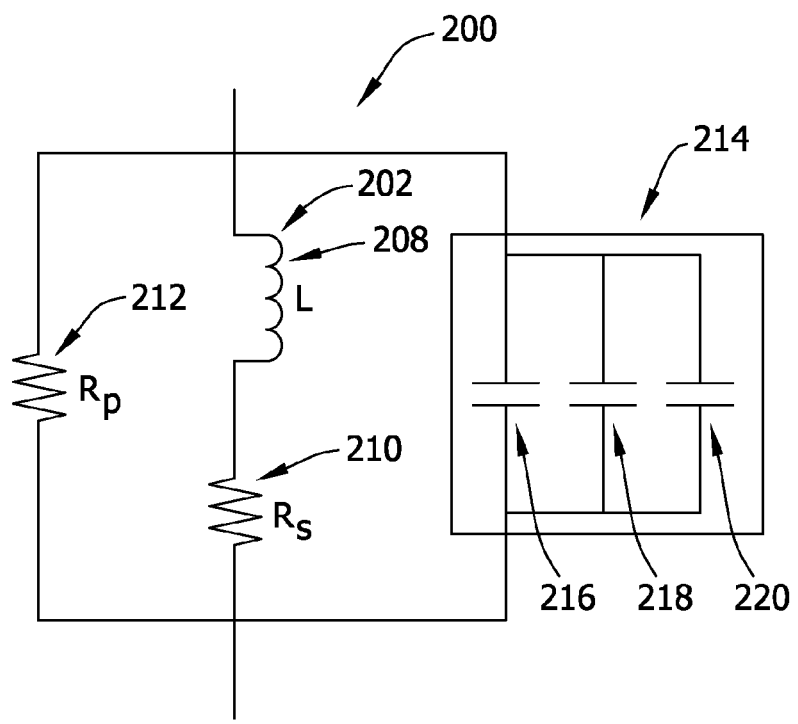
FIG. 2B is a schematic view of a circuit representing electrical characteristics of the sensor of FIG. 2A.

FIGS. 2A and 2B illustrate a sensor 104 suitable for use with the monitoring system 100 shown in FIG. 1. More specifically, FIG. 2A is a top view of the sensor 104, and FIG. 2B is a schematic view of a circuit 200 representative of the electrical characteristics of the sensor.

As seen in FIG. 2A, the sensor 104 includes a sensor body 206 having a substantially planar surface 204. A substantially spiral-shaped conductor 202 (or "coil") is coupled to the substantially planar surface 204 of the sensor body 206. In one suitable embodiment, the sensor body 206 is a printed circuit board (PCB). For example, the sensor body 206 may be a dual-layer PCB that includes the conductor 202 positioned within a first layer and an additional conductor (not shown) arranged in a spiral shape, staggered or interleaved with respect to the conductor 202, and positioned within the second layer. In other embodiments, the sensor body 206 can be other substrates that enable the conductor 202 to be coupled thereto.

As seen in FIG. 2B, the conductor 202 is represented as an inductor 208 (L) coupled in series with a first resistive element 210 ($R_s$). The conductor 202 and the first resistive element 210 are coupled in parallel with a second resistive element 212 ($R_p$) and a capacitive element 214.

In one suitable embodiment, the first resistive element 210 represents an effective resistance added or induced into the sensor 104 as a result of the eddy currents interacting with the object 102. The second resistive element 212 is a resistor coupled to the sensor 104 to reduce a "Q" factor of the sensor 104 as desired. It should be recognized that, while the second resistive element 212 may be selected to have any suitable resistance, the second resistive element has a much higher resistance than the resistance of the first resistive element 210. For example, the second resistive element 212 may have a resistance that is about 1,000 times higher, 10,000 times higher, or even higher, than the resistance of the first resistive element 210.

The capacitive element 214 is coupled to the sensor 104 to adjust a phase angle of the signal received from the sensor and/or the current flowing through the sensor. In one suitable embodiment, the capacitive element 214 is an adjustable capacitor (also known as a "trimmer") that enables a user or a device such as the controller 108 to adjust the capacitance of the capacitive element 214. It should be recognized that the capacitive element 214 may be represented as a plurality of capacitive components coupled together in parallel. For example, a first capacitive component 216 represents an amount of capacitance attributed to the conductor 202, a second capacitive component 218 represents a capacitance shunted across the conductor 202 as a result of an interaction with the conductor 202 and an object 102 positioned proximate to the conductor 202, and a third capacitive component 220 represents the adjustable capacitance described above that enables the user or the controller 108 to adjust the capacitance of the capacitive element 214.

In one suitable embodiment, the monitoring system 100 measures the shunted capacitance across the conductor 202 (i.e., the capacitance represented by the second capacitive component 218). The user or controller 108 adjusts or "sweeps" the value of the capacitive element 214 (i.e., third capacitive component 220) throughout a capacitance range of the capacitive element 214 while measuring a phase angle (or a corrected phase angle as described below) of the signal received from the sensor 104 at each capacitance value. The adjustment of the capacitive element 214 (also referred to as a "capacitive sweep") is performed a first time with the object near the conductor 202 (i.e., within the electromagnetic field 114 generated by the conductor) and a second time without the object near the conductor (i.e., not within the electromagnetic field generated by the conductor). The controller 108 compares the capacitance values required to produce resonance (e.g., a phase angle of substantially zero) during the two capacitive sweeps to determine a difference between the capacitances. An amount of capacitance required to produce resonance when no object is near the conductor 202 is more than the amount of capacitance required when the object is near the conductor. The difference in capacitance values is the amount of capacitance arising from the interaction between the conductor 202 and the object 102, and is further related to the physical condition or state of the object.

Figure 3:
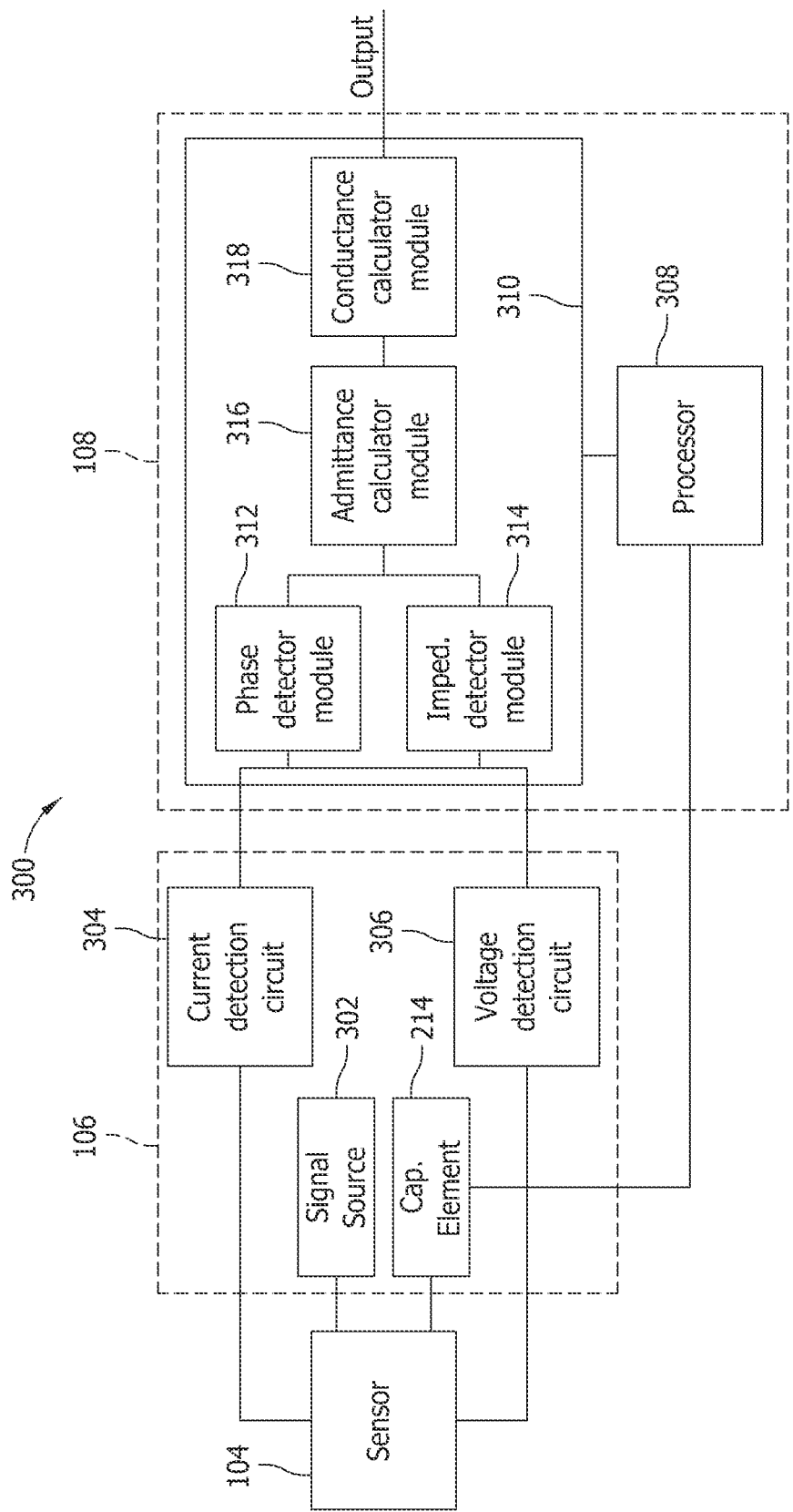
FIG. 3 is a block diagram of the monitoring system illustrated in FIG. 1.
Figure 4:
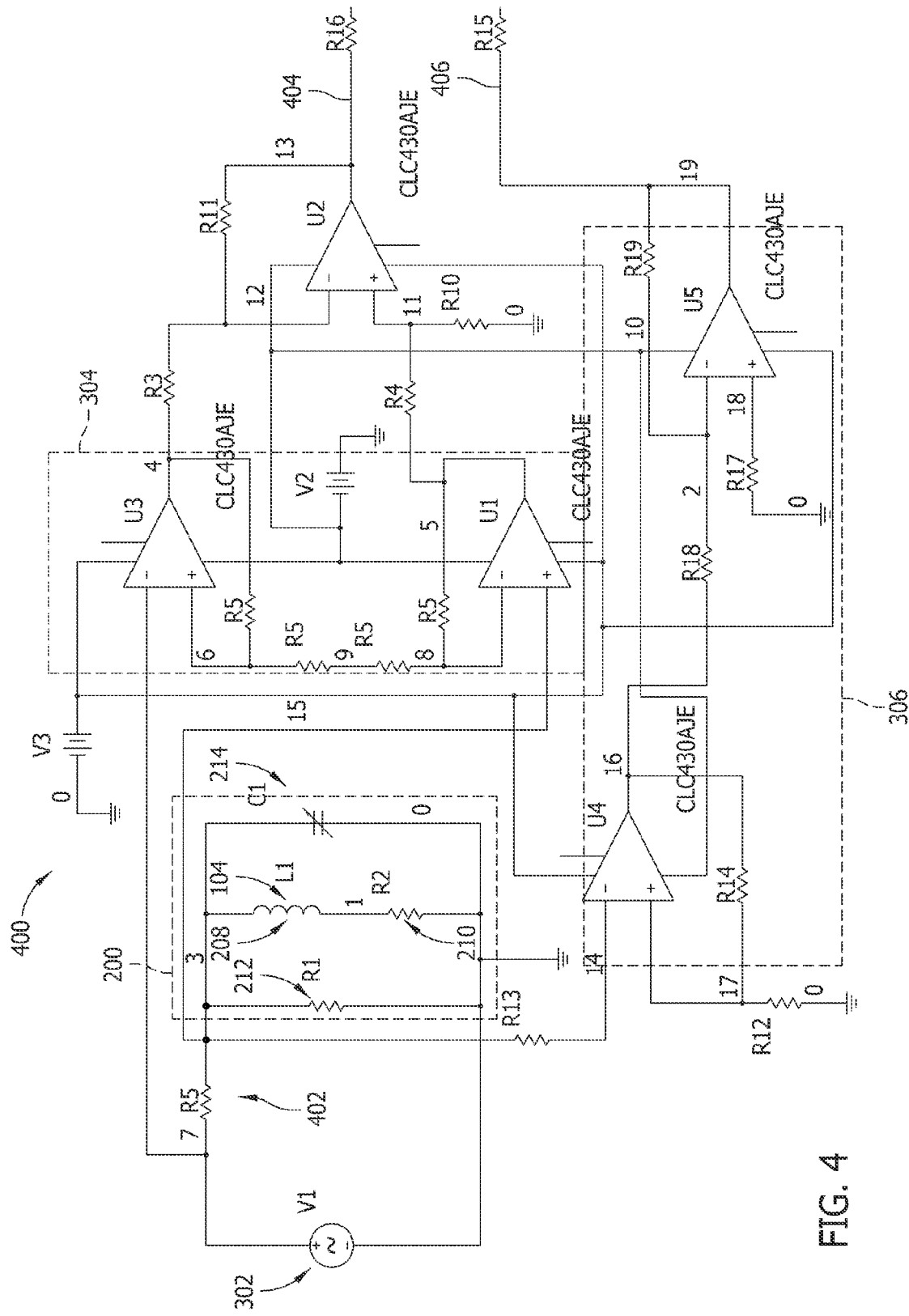
FIG. 4 is a schematic diagram of an analog portion of a signal processing circuit suitable for use with the monitoring system illustrated in FIG. 3.

FIG. 3 is a simplified block diagram, indicated generally at 300, of the monitoring system 100 shown in FIG. 1. FIG. 4 schematically illustrates an analog portion of one exemplary signal processing circuit 400 of the monitoring system 100.

As seen in FIG. 3, the sensor 104 is coupled to the capacitive element 214 and to a signal source 302. In one suitable embodiment, the capacitive element 214 and the signal source 302 are positioned within the signal processing circuit 106. Alternatively, the capacitive element 214 and/or the signal source 302 may be positioned within the sensor 104 or external to both the sensor and the signal processing circuit 106.

The signal processing circuit 106 includes a current detection circuit 304 and a voltage detection circuit 306. The current detection circuit 304 detects or measures a current flowing through, or output from, the sensor 104. In one suitable embodiment, the current detection circuit 304 generates an output signal (hereinafter referred to as a "current measurement signal") having a voltage that is proportional to the measured current flowing through the sensor 104. The voltage detection circuit 306 detects or measures a voltage across the sensor 104, or a voltage output from the sensor. In a suitable embodiment, the voltage detection circuit 306 generates an output signal (hereinafter referred to as a "voltage measurement signal") having a voltage that is proportional to the measured voltage across the sensor 104. The current measurement signal and the voltage measurement signal are transmitted to the controller 108.

The controller 108 includes a processor 308 and a memory device 310 operatively connected to the processor. The processor 308 includes any suitable programmable circuit including one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the meaning of the term "processor". In a suitable embodiment, the processor 308 is operatively coupled to the capacitive element 214 to control or adjust the capacitance of the capacitive element.

The memory device 310 includes a computer readable storage medium, such as, without limitation, random access memory (RAM), flash memory, a hard disk drive, a solid state drive, a diskette, a flash drive, a compact disc, a digital video disc, and/or any suitable memory. In a suitable embodiment, the memory device 310 includes data and/or instructions that are executable by the processor 308 such that the processor 308 is programmed by the instructions to enable the processor 308 to perform the functions described herein.

In addition, the memory device 310 includes a plurality of computer-executable program modules that are executed by the processor 308. The program modules include a phase detector module 312, an impedance detector module 314, an admittance calculator module 316, and a conductance calculator module 318. Alternatively, one or more of the program modules, such as the phase detector module 312, may be implemented by a circuit or a device separate from the processor 308.

In a suitable embodiment, the phase detector module 312 detects a phase angle of the sensor 104 (e.g., of the current flowing through the sensor) based on the current measurement signal and the voltage measurement signal received from the signal processing circuit 106. Specifically, the phase detector module 312 detects a phase shift or phase angle between the current measurement signal and the voltage measurement signal, and generates a signal or value (hereinafter referred to as a "sensor phase angle") representative of the detected phase shift or phase angle between the voltage measurement signal and the current measurement signal. In one suitable embodiment, as described more fully herein, the processor 308 calculates a phase angle correction value for adjusting the sensor phase angle.

The impedance detector module 314 detects an effective impedance of the sensor 104 (e.g., an impedance of the effective sensor circuit 200 shown in FIG. 2B). Specifically, the impedance detector module 314 divides the root mean square (RMS) voltage measured across the sensor 104 (hereinafter referred to as the "sensor voltage"), as represented by the voltage measurement signal, by the RMS current flowing through the sensor (hereinafter referred to as the "sensor current"), as represented by the current measurement signal, to obtain the effective impedance of the sensor (hereinafter referred to as the "sensor impedance"). In some embodiments, the sensor voltage and the sensor current can be based on instantaneous voltage and current values obtained from a waveform of the voltage across the sensor 104 and the current flowing through the sensor.

The admittance calculator module 316 calculates the admittance of the sensor 104 based on the sensor phase angle (as adjusted by the phase angle correction value) and the sensor impedance. For example, as described more fully herein, the admittance calculator module 316 calculates the admittance of the sensor by dividing the cosine of the sensor phase angle (as adjusted by the phase angle correction value) by the sensor impedance.

The conductance calculator module 318 determines or calculates a conductance of the object 102 based on the calculated admittance of the sensor 104. For example, in a suitable embodiment, the conductance calculator module 318 determines the conductance of the object 102 by referencing a calibration plot, described more fully herein, to determine the conductance value corresponding to the calculated admittance value of the sensor 104. The conductance of the object 102, the admittance of the sensor 104, and/or any other values determined or calculated by the controller 108 may be output, for example, to a display or to a storage device.

As illustrated in FIG. 4, the signal source 302 is coupled in parallel with the second resistive element 212, the capacitive element 214, and the sensor circuit 200 (including inductor 208 and first resistive element 210) that are described above with reference to FIG. 2B. The signal source 302 is also coupled in series with a current sense resistor 402 for use in detecting the current flowing through sensor 104 (i.e., the sensor current described above). The signal source 302 is an alternating current (AC) source that provides an AC excitation signal to sensor 104. In one suitable embodiment, the signal source 302 is, or includes, a Colpitts crystal oscillator that oscillates at a predetermined frequency, such as at about 12 megahertz (MHz) or at any other suitable frequency.

In a suitable embodiment, the current detection circuit 304 is coupled across the current sense resistor 402 to measure the voltage drop across the current sense resistor. In one suitable embodiment, the current detection circuit 304 includes a pair of amplifiers, such as a pair of operational amplifiers (op-amps). The current detection circuit 304 generates a first output 404 of the signal processing circuit 400 (i.e., the current measurement signal) that has a voltage proportional to the current flowing through sensor 104.

In a suitable embodiment, the voltage detection circuit 306 is coupled across the second resistive element 212 to measure the voltage drop across the second resistive element 212, and therefore, the voltage drop across the sensor 104. In one suitable embodiment, the voltage detection circuit 306 includes a pair of amplifiers, such as a pair of op-amps. The voltage detection circuit 306 generates a second output 406 of the signal processing circuit 400 (i.e., the current measurement signal) that has a voltage proportional to the voltage across sensor 104.

During operation, signal processing circuit 400 is used to facilitate determining the conductance of the object 102 by calculating the admittance of the sensor 104. Specifically, the admittance (Y) of the sensor 104 is:

$$Y = G + jB \qquad \text{Equation 1}$$

where G is the real part of the admittance Y, and B is the imaginary part (susceptance) of the admittance Y. In a suitable embodiment, only the real part G of the admittance is used herein, and the imaginary part B of the admittance is disregarded. Accordingly, as used herein, the term "admittance" refers to the real part G of the admittance Y, unless otherwise specified.

The admittance G of the sensor 104 is obtained by computing G from the equation:

$$G = \frac{\cos\theta}{|Z|} = \frac{1}{R_p} + \frac{R_s}{R_s^2 + \omega^2 L^2} \qquad \text{Equation 2}$$

where θ is the phase angle of the sensor (i.e., the phase angle of the signal output from the sensor), Z is the impedance of the sensor, $R_p$ is the resistance of the second resistive element 212, $R_s$ is the effective resistance of the first resistive element 210, ω is the frequency of the sensor (i.e., the frequency of the signal output from the sensor), and L is the inductance of sensor (i.e., of inductor 208).

Referring to Equation 2, $R_s$ is typically small in comparison to the term $\omega^2 L^2$ and, in some embodiments, may be disregarded, or approximated to be zero next to the term $\omega^2 L^2$. Accordingly, as the inductance L is constant, the admittance is modeled to be substantially linear with respect to $1/\omega^2$. In other words, the admittance of the sensor 104 can be calculated at many suitable frequencies, and, in contrast to prior art systems, is not limited to only being calculated at or near a resonance frequency, or in a resonant state, of the sensor 104.

Accordingly, to calculate the admittance of the sensor 104, the sensor phase angle and the sensor impedance are calculated as described above. The processor 308 calculates the cosine of the sensor phase angle and divides the result by the sensor impedance to calculate the admittance of the sensor.

However, the measurement of the phase angle may need to be adjusted or calibrated due to additional phase shifting resulting from other circuit components. Accordingly, in a suitable embodiment, a phase angle correction value is determined before calculating the admittance of the sensor 104. First, the capacitive element 214 is adjusted to a high capacitive value, such as a highest capacitive value that the capacitive element is able to provide. The phase angle (hereinafter referred to as the "high capacitance phase angle") of the sensor 104 is measured as described above, and the phase angle correction value is set to about 90 degrees plus the high capacitance phase angle. In an ideal situation with ideal components, the phase angle correction value would be zero.

The capacitive element 214 is then adjusted (i.e., the capacitance coupled across the sensor 104 is adjusted) until the phase angle of the sensor minus the phase angle correction value is within a predefined phase angle window. In one suitable embodiment, the phase angle window is between about −70 degrees and about +70 degrees. In a further embodiment, the phase angle window excludes a predefined resonance phase angle window that is between about −3 degrees and about +3 degrees. Accordingly, in such an embodiment, the phase angle window may include phase angles between about −70 degrees and about −3 degrees, and between about +3 degrees and about +70 degrees. Alternatively, the phase angle window and/or the resonance phase angle window may include any other upper or lower boundaries to enable the monitoring system 100 to function as described herein.

When the phase angle, as adjusted by the phase angle correction value (i.e., the phase angle minus the phase angle correction value) is within the predefined phase angle window, the processor 308 calculates the admittance of the sensor 104 as described above, e.g., by dividing the cosine of the adjusted sensor phase angle by the sensor impedance. The processor 308 determines the conductance of the object 102 by referencing a calibration plot of the sensor 104. Accordingly, as described herein, the monitoring system 100 (e.g., the processor 108) may calculate the admittance of the sensor 104 and may determine the conductance of the object 102 while the sensor is not in a resonant state.

Figure 5:
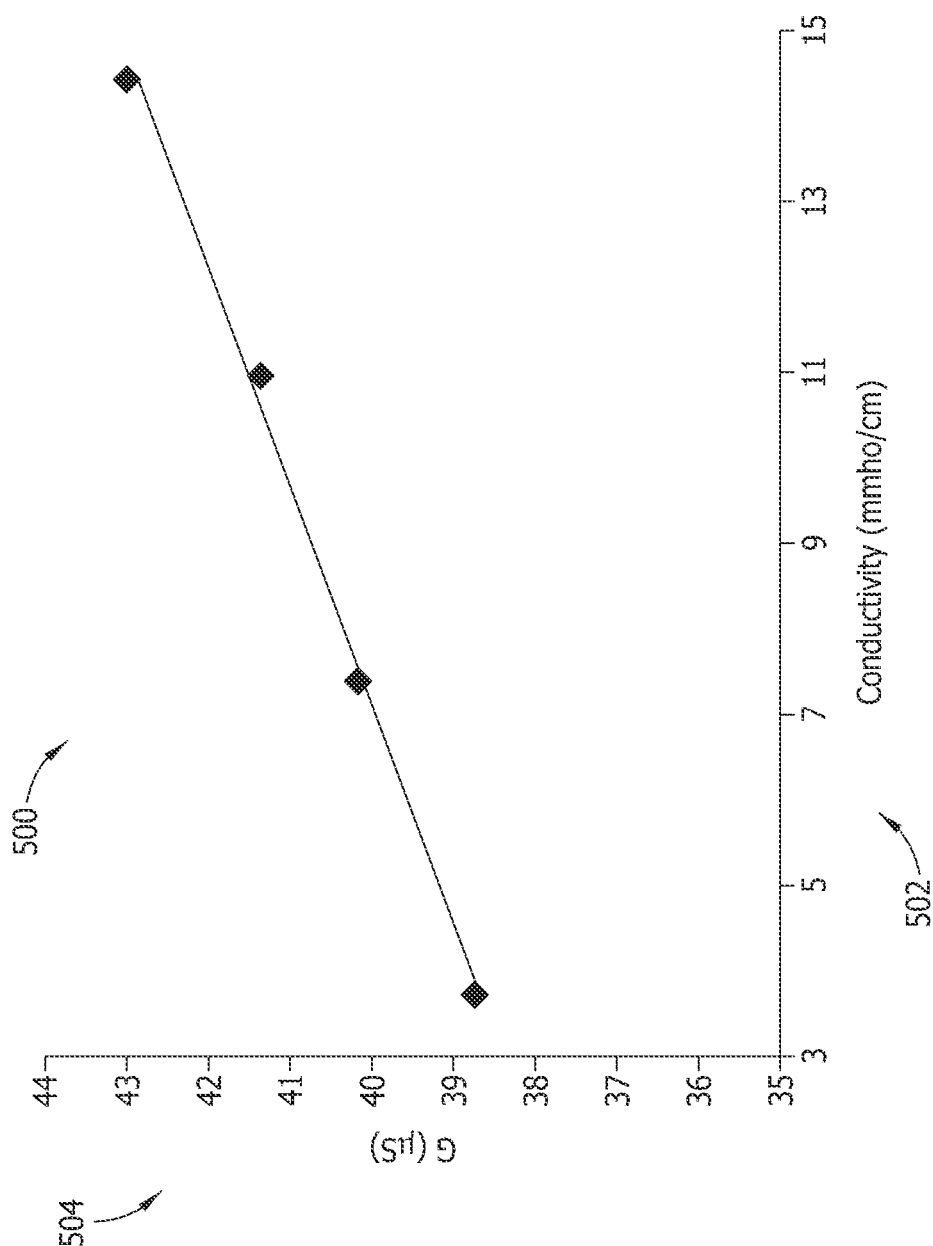
FIG. 5 is a graph of a calibration plot that can be generated and used by the monitoring system.

FIG. 5 graphically illustrates an exemplary calibration plot, indicated generally at 500, that may be generated and/or used by the monitoring system 100. The abscissa axis of calibration plot 500 represents a conductance (or conductivity) 502 of one or more objects, and the ordinate axis represents an admittance 504 of the sensor 104 as determined by the monitoring system 100. In a suitable embodiment, all measurements represented within the calibration plot 500 are obtained using a single fixed frequency for the sensor excitation signal.

In a suitable embodiment, the calibration plot 500 is generated to calibrate the monitoring system 100. For example, the calibration plot 500 is generated to identify the correlation between the measured admittance 504 of the sensor 104 and the conductance 502 of the standardized objects monitored. Experimental results indicate that there is a substantially linear relationship between the admittance 504 of the sensor 104 and the inverse of the square of the signal frequency output from the sensor 104 when the conductivity of the monitored object is fixed. Furthermore, experimental results also indicate that there is a substantially linear relationship between the admittance 504 of the sensor 104 and the conductivity (or conductance 502) of the monitored object when the excitation frequency is maintained at a fixed frequency, such as when the monitoring system 100 is used as described herein.

During operation, a plurality of objects having known conductances (i.e., the objects are composed of materials having known conductances) are selected and monitored by the monitoring system 100. Each object is selected such that a conductance of each object is different from a conductance of each other object. For each object, the monitoring system 100 emits the electromagnetic field 114 towards the object and calculates the admittance of the sensor 104 (as described above with reference to FIGS. 3 and 4) in response to eddy currents induced within the object. For each measurement, the gap between the sensor and the object (i.e., the gap 112 shown in FIG. 1) is maintained at substantially the same distance. The measured admittances are plotted against the known specific conductance of the objects, and the calibration plot 500 is generated by utilizing a best-fit algorithm or otherwise generating a line substantially connecting each of the plotted admittance 504 and conductance 502 values. In some suitable embodiments, a plurality of calibration plots 500 corresponding to measurements taken at a plurality of gaps 112 are generated and stored in a memory, such as the memory device 310 shown in FIG. 3).

When the calibration plot 500 has been generated, a slope of the plot 500 and a zero crossing of the plot 500 (i.e., an intercept, or a value of the admittance 504 when the object conductance 502 is zero) are determined. The slope and the zero crossing of the calibration plot 500 enable a later correlation between a measured admittance 504 of the sensor 104 and an unknown conductance 502 of an object monitored by the monitoring system 100.

Figure 6:
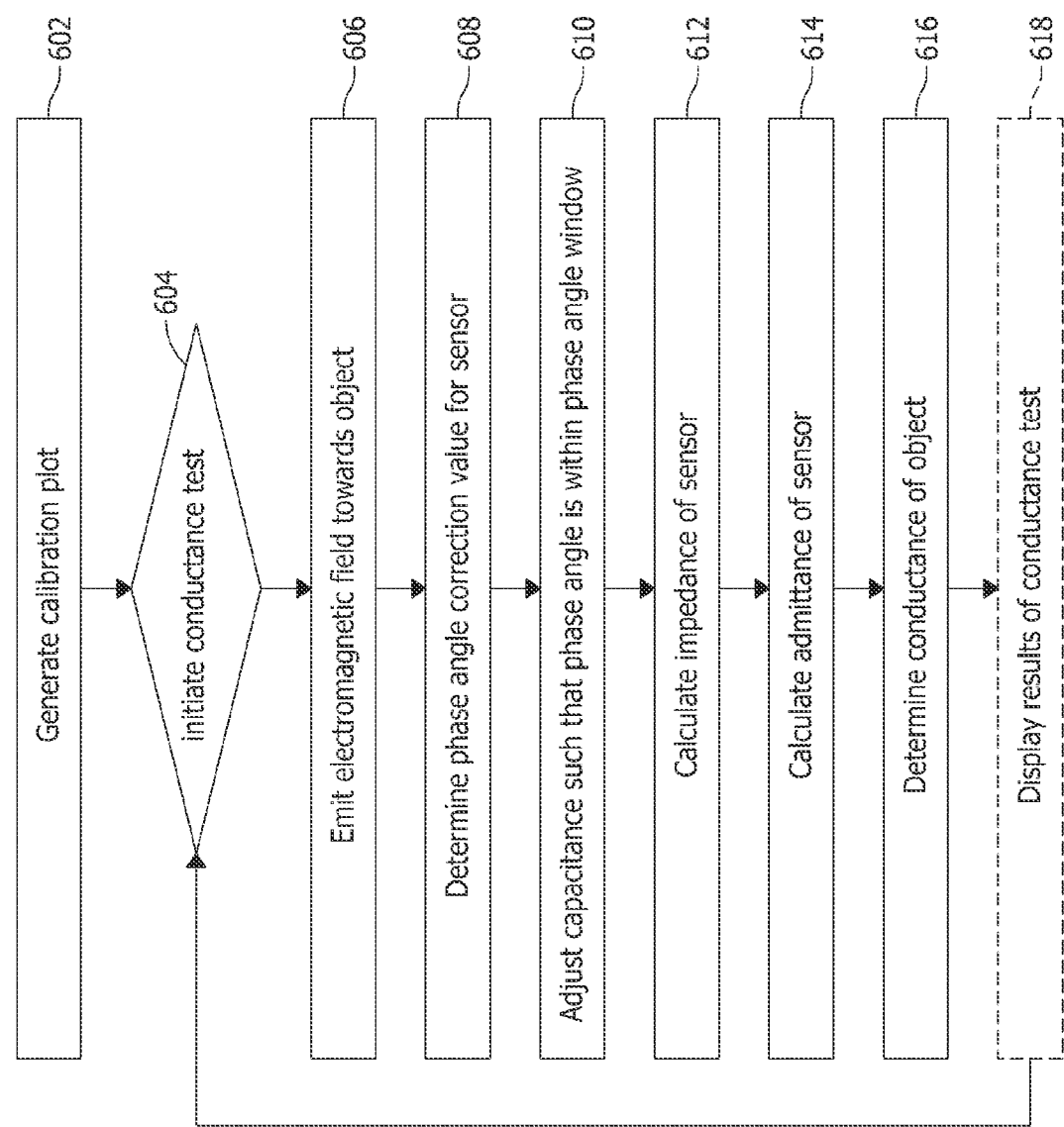
FIG. 6 is a flowchart illustrating a method of determining a conductance of an object using the monitoring system.

FIG. 6 is a flowchart illustrating a suitable method 600 of determining a conductance of an object, such as the object 102 shown in FIG. 1. In a suitable embodiment, the method 600 is executed by the monitoring system 100 shown in FIG. 1.

Initially, a calibration plot 500 is generated 602 for the monitoring system 100. For example, admittance values of the sensor 104 are calculated or measured while using the sensor to monitor objects having known conductance, as described more fully above with reference to FIG. 5. The calibration plot 500 is generated from the measured admittance values and the known conductance values. In one suitable embodiment, the calibration plot 500 and/or the values that the calibration plot is based on are stored in a memory, such as the memory device 310 of the monitoring system 100. In some embodiments, a plurality of calibration plots 500 corresponding to measurements taken at a plurality of gaps 112 are generated and stored in the memory device 310.

After the calibration plot 500 is generated 602, a conductance test may be initiated 604. An electromagnetic field 114 is emitted 606 towards the object 102, and the field interacts with the object. A phase angle correction value is determined 608 for the sensor 104, for example, as described above with reference to FIG. 4. Moreover, a capacitance of the sensor 104 (e.g., the capacitive element 214 shown in FIG. 2) is adjusted 610 such that the sensor phase angle (minus the phase angle correction value) is within the phase angle window. In one suitable embodiment, values representative of the sensor current, the sensor voltage, the sensor phase angle, and the phase angle correction value are stored in memory.

An impedance of the sensor 104 is calculated 612 using the sensor current and the sensor voltage values. An admittance of the sensor 104 is calculated 614 using the calculated impedance and the adjusted sensor phase angle (i.e., the sensor phase angle minus the phase angle correction value).

A conductance of the object 102 is determined 616 based on the calculated admittance of the sensor 104 and based on a calibration plot 500. For example, the calculated admittance of the sensor 104 is plotted on the calibration plot 500 and a corresponding conductance value for the object 102 is determined. The results of the conductance test may optionally be displayed 618, such as the calculated admittance of the sensor 104, the determined conductance of the object 102, and/or any other value determined using the method 600 or the monitoring system 100. The results may also include a comparison to prior test results to determine a change in the admittance and/or conductivity, and/or may include a comparison to one or more baseline values, such as a baseline admittance or conductance value. The results may be displayed to a user on a display device, may be transmitted electronically to one or more remote devices to be displayed, and/or may be stored in a memory for later display and/or analysis. The method 600 returns to initiating 604 a new conductance test for the object 102 or for a new object as desired.

Figure 7:
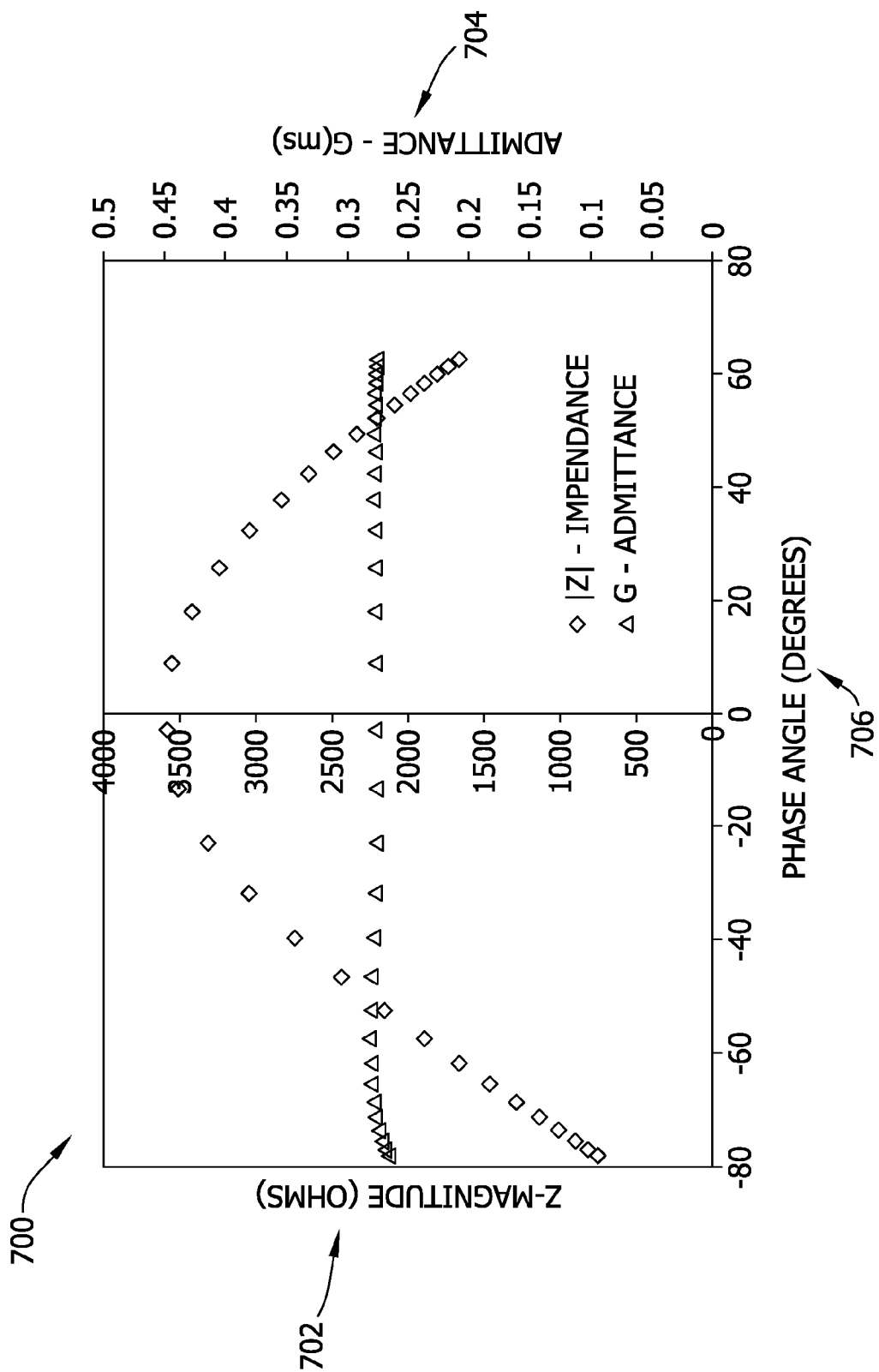
FIG. 7 is a graph of an admittance of the object measured by the monitoring system.

FIG. 7 graphically illustrates a measured admittance, indicated generally at 700, as experimentally generated by the monitoring system 100. The first ordinate axis of admittance plot 700 represents a calculated impedance 702 of an object, and the second ordinate axis represents a calculated admittance 704 of the object. The abscissa axis represents a phase angle 706 of the sensor 104.

The admittance plot 700 includes experimental data illustrating that the computed value of admittance is substantially constant through the range of phase angle values (e.g., between about −70 degrees and about 70 degrees) despite the impedance varying considerably as the phase angle changes. It should be recognized that, in one embodiment, a phase angle correction is not needed for sensor 104 and/or signal processing circuit 106 since the calculated impedance reaches a maximum value at a phase angle of about zero, which is indicative of resonance.

Alternatively, the phase angle may be corrected by tuning the signal processing circuit 106, by adjusting capacitive element 214, until a maximum value of the impedance is reached (as illustrated in FIG. 7). The phase angle measured at the point at which the impedance is maximized is used as a phase angle correction value. Accordingly, in such an embodiment, the value of the phase angle identified at the maximum impedance value is subtracted from subsequent phase angle measurements. While the phase angle may not need to be corrected, it may be desirable to deliberately introduce a phase shift within the current detection circuit 304 or the voltage detection circuit 306, for example. Such a phase shift may improve phase measurement accuracy, especially when operating monitoring system 100 with a phase angle of zero or close to zero A technical effect of the systems and methods described herein includes at least one of (a) emitting an electromagnetic field towards an object such that the electromagnetic field interacts with the object; (b) adjusting a phase angle of a current flowing through the sensor using an adjustable capacitive element coupled to the sensor; (c) generating a voltage measurement representative of a voltage across the sensor; (d) generating a current measurement representative of the current flowing through the sensor; (e) calculating an admittance of the sensor based on the voltage measurement and the current measurement; and (f) determining a conductance of the object based on the calculated admittance of the sensor.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A system for determining a conductance of an object, the system comprising:
   a sensor configured to emit an electromagnetic field when an excitation signal is received, wherein the electromagnetic field interacts with the object when the object is positioned within the electromagnetic field;

a signal processing circuit coupled to the sensor and configured to:
provide an adjustable capacitance to the sensor to adjust a phase angle of a current flowing through the sensor;
generate a voltage measurement representative of a voltage across the sensor; and
generate a current measurement representative of the current flowing through the sensor; and
a controller coupled to the signal processing circuit, the controller configured to:
adjust the adjustable capacitance to drive the sensor to a non-resonant state;
calculate an admittance of the sensor based on:
the voltage measurement when the sensor is in the non-resonant state; and
the current measurement when the sensor is in the non-resonant state; and
determine a conductance of the object based on the calculated admittance of the sensor.

2. The system as set forth in claim 1, wherein the controller further comprises a memory device, the controller being configured to store data representative of a calibration plot within the memory device, wherein the calibration plot includes a correlation of prior admittance values of the sensor and conductance values of a plurality of known materials.

3. The system as set forth in claim 2, wherein the controller determines the conductance of the object by correlating the calculated admittance of the sensor with a conductance value using the calibration plot.

4. The system as set forth in claim 1, wherein the controller is configured to calculate the admittance of the sensor by calculating a real part of the admittance of the sensor and disregarding an imaginary part of the admittance of the sensor.

5. The system as set forth in claim 1, wherein the controller is configured to determine a phase angle of the current flowing through the sensor and an impedance of the sensor based on the voltage measurement and the current measurement generated.

6. The system as set forth in claim 5, wherein the controller is configured to calculate a phase angle correction value for the phase angle of the current flowing through the sensor.

7. The system as set forth in claim 6, wherein the controller is configured to adjust the capacitance such that the phase angle minus the phase angle correction value is within a predefined phase angle window.

8. The system as set forth in claim 7, wherein the predefined window excludes a resonance phase angle window such that the signal processing circuit causes the system to determine the conductance of the object while the sensor is not in a resonant state.

9. The system as set forth in claim 1, wherein the controller is further configured to determine a capacitance shunted across the sensor as a result of an interaction with the object.

10. The system as set forth in claim 9, wherein the controller is configured to determine the capacitance by:
adjusting the adjustable capacitance to a first value to cause the sensor to be in a resonant state when the object is not positioned within the electromagnetic field;
adjusting the adjustable capacitance to a second value to cause the sensor to be in a resonant state when the object is positioned within the electromagnetic field; and
determining the capacitance shunted across the sensor to be a difference between the first value and the second value.

11. A method of determining a conductance of an object comprising:
emitting an electromagnetic field from a sensor towards an object such that the electromagnetic field interacts with the object;
adjusting a phase angle of a current flowing through the sensor to drive the sensor to a non-resonant state using a processor to adjust an adjustable capacitive element coupled to the sensor;
generating a voltage measurement representative of a voltage across the sensor;
generating a current measurement representative of the current flowing through the sensor;
calculating an admittance of the sensor based on:
the voltage measurement when the sensor is in the non-resonant state; and
the current measurement when the sensor is in the non-resonant state; and
determining a conductance of the object based on the calculated admittance of the sensor.

12. The method as set forth in claim 11, further comprising storing data representative of a calibration plot within a memory device, wherein the calibration plot includes a correlation of prior admittance values of the sensor and conductance values of a plurality of known materials.

13. The method as set forth in claim 12, further comprising determining the conductance of the object by correlating the calculated admittance of the sensor with a conductance value using the calibration plot.

14. The method as set forth in claim 11, further comprising calculating the admittance of the sensor by calculating a real part of the admittance of the sensor and disregarding an imaginary part of the admittance of the sensor.

15. The method as set forth in claim 11, further comprising determining a phase angle of the current flowing through the sensor and an impedance of the sensor based on the voltage measurement and the current measurement generated.

16. The method as set forth in claim 15, further comprising calculating a phase angle correction value for the phase angle of the current flowing through the sensor.

17. The method as set forth in claim 16, further comprising adjusting the capacitive element such that the phase angle minus the phase angle correction value is within a predefined phase angle window.

18. The method as set forth in claim 17, further comprising determining the conductance of the object while the sensor is not in a resonant state.

19. A controller for determining a conductance of an object, the controller comprising:
a processor; and
a memory device coupled to the processor and configured to store a plurality of program modules comprising:
a phase angle calculator module executable by the processor to:
receive a current measurement representative of a current flowing through a sensor when the sensor is in a non-resonant state;

receive a voltage measurement representative of a voltage across the sensor when the sensor is in the non-resonant state; and calculate a phase angle of the current flowing through the sensor based on the current measurement and the voltage measurement;

an impedance calculator module executable by the processor to:

receive the current measurement;

receive the voltage measurement; and calculate an impedance of the sensor based on the current measurement and the voltage measurement;

an admittance calculator module executable by the processor to calculate an admittance of the sensor based on:

the calculated phase angle when the sensor is in the non-resonant state; and the calculated impedance when the sensor is in the non-resonant state; and a conductance calculator module executable by the processor to determine a conductance of the object based on the calculated admittance of the sensor.

20. The controller as set forth in claim 19, wherein the processor is configured to calculate a phase angle correction value for the phase angle of the current flowing through the sensor.

21. The controller as set forth in claim 20, wherein the admittance calculator module is executable by the processor to:

subtract the phase angle correction value from the phase angle to obtain an adjusted phase angle value; and calculate the admittance of the sensor based on the impedance of the sensor and the adjusted phase angle value.

22. The controller as set forth in claim 19, wherein the controller is configured to adjust a capacitance of the sensor to drive the sensor to the non-resonant state.

* * * * *